United States Patent
Orlowski et al.

(10) Patent No.: US 7,067,115 B2
(45) Date of Patent: *Jun. 27, 2006

(54) PROCESS AND COMPOSITION FOR HIGH EFFICACY TEETH WHITENING

(75) Inventors: Jan A. Orlowski, Altadena, CA (US); David V. Butler, West Covina, CA (US)

(73) Assignee: Scientific Pharmaceuticals, Inc., Pomona, CA (US)

( * ) Notice: Subject to any disclaimer, the term of this patent is extended or adjusted under 35 U.S.C. 154(b) by 107 days.

This patent is subject to a terminal disclaimer.

(21) Appl. No.: 10/125,787

(22) Filed: Apr. 17, 2002

(65) Prior Publication Data

US 2003/0044360 A1 Mar. 6, 2003

Related U.S. Application Data

(63) Continuation-in-part of application No. 10/114,436, filed on Apr. 1, 2002, now abandoned, which is a continuation of application No. 09/618,567, filed on Jul. 17, 2000, now Pat. No. 6,365,134, which is a continuation of application No. 09/348,456, filed on Jul. 7, 1999, now abandoned.

(51) Int. Cl.
*A61K 7/16* (2006.01)
*A61K 7/20* (2006.01)

(52) U.S. Cl. .............. 424/53; 424/52; 433/90; 433/141; 433/164; 433/215; 433/216

(58) Field of Classification Search ............ 424/52, 424/53; 433/90, 141, 164, 215, 216
See application file for complete search history.

(56) References Cited

U.S. PATENT DOCUMENTS

| | | |
|---|---|---|
| 3,499,844 A | 3/1970 | Kibbel, Jr. et al. |
| 3,607,759 A | 9/1971 | Barth |
| 3,657,413 A | 4/1972 | Rosenthal et al. |
| 4,032,627 A | 6/1977 | Suchan et al. |
| 4,405,599 A | 9/1983 | Smigel |
| 4,522,805 A | 6/1985 | Gordon |
| 4,661,070 A | 4/1987 | Friedman |
| 4,687,663 A | 8/1987 | Schaeffer |
| 4,788,052 A | 11/1988 | Ng et al. |
| 4,839,156 A | 6/1989 | Ng et al. |
| 4,895,721 A | 1/1990 | Drucker |
| 4,897,258 A | 1/1990 | Rudy et al. |
| 4,971,782 A | 11/1990 | Rudy et al. |
| 4,976,955 A | 12/1990 | Libin |
| 4,980,152 A | 12/1990 | Frazier et al. |
| 4,980,154 A | 12/1990 | Gordon |
| 4,983,379 A | 1/1991 | Schaeffer |
| 4,983,380 A | 1/1991 | Yarborough |
| 4,983,381 A | 1/1991 | Torres Zaragoza |
| 4,990,089 A | 2/1991 | Munro |
| 5,000,942 A | 3/1991 | Libin |
| 5,032,178 A | 7/1991 | Cornell |
| 5,041,280 A | 8/1991 | Smigel |
| 5,076,791 A | 12/1991 | Madray, Jr. |
| 5,084,268 A | 1/1992 | Thaler |
| 5,089,254 A * | 2/1992 | Coulson ............ 426/52 |
| 5,098,303 A | 3/1992 | Fischer |
| 5,122,365 A | 6/1992 | Murayama |
| 5,171,564 A | 12/1992 | Nathoo et al. |
| RE34,196 E | 3/1993 | Munro |
| 5,208,010 A | 5/1993 | Thaler |
| 5,234,342 A | 8/1993 | Fischer |
| 5,240,415 A | 8/1993 | Haynie |
| 5,256,402 A | 10/1993 | Prencipe et al. |
| 5,264,205 A | 11/1993 | Kelly |

(Continued)

FOREIGN PATENT DOCUMENTS

| | | |
|---|---|---|
| GB | 2117240 | 10/1983 |
| WO | 97/07777 | 3/1997 |
| WO | 97/11676 | 4/1997 |
| WO | 98/23219 | 6/1998 |
| WO | 98/31331 | 7/1998 |
| WO | 99/20226 | 4/1999 |

OTHER PUBLICATIONS

Council on Scientific Affairs, ADA, "Home–Use Tooth Whitening Products", Jan. 1998/DRAFT, pp 1–15.

Daytime ZERO Sensitivity Tooth Whitening, Day White 2 "Z" 7.5% Hydrogen Peroxide Tooth Whitening Gel, Discuss Dental, Inc., Culver City, CA : www.discusdental.com (1998).

Nite White Excel 2, Discuss Dental, Inc., Culver City. CA : www.discusdental.com (1998).

Opalescence PF Tooth Whitening Gel, Ultradent Products, Inc., May 1999.

A Reason to Smile, Opalescence Tooth Whitening System, Ultradent Products, Inc, Oct., 1998.

Opalscence Dentist Instructions and MSDS, Ultradent Products, Inc., Jun., 1997.

*Primary Examiner*—Frederick F. Krass
(74) *Attorney, Agent, or Firm*—Knobbe, Martens, Olson & Bear, LLP

(57) ABSTRACT

Disclosed is a process and composition for bleaching teeth made up of two components blended together before each application. The method and composition offers faster results while significantly reducing the possibility of user discomfort. One of said components comprises carbamide peroxide, the other contains salts and hydroxides and/or oxides of metals belonging to the first or second group of the Periodic Table which stimulate the generation of radical oxygen. In one embodiment, the first part comprises up to 50% water by weight and optionally comprises a stabilizer. In some embodiments, the first component is substantially colorless and the second component comprises a dye indicator which discolors or loses color when exposed to radical oxygen generated by the mixing of the two components.

38 Claims, No Drawings

U.S. PATENT DOCUMENTS

| | | |
|---|---|---|
| 5,290,566 A | 3/1994 | Schow et al. |
| 5,302,374 A | 4/1994 | Wagner |
| 5,356,291 A | 10/1994 | Darnell |
| 5,376,006 A | 12/1994 | Fischer |
| 5,401,495 A | 3/1995 | Murayama |
| 5,409,631 A | 4/1995 | Fischer |
| 5,425,953 A | 6/1995 | Sintov et al. |
| 5,437,858 A | 8/1995 | Hungerbach et al. |
| 5,597,554 A | 1/1997 | Wagner |
| 5,631,000 A | 5/1997 | Pellico et al. |
| 5,645,428 A | 7/1997 | Yarborough |
| 5,645,821 A | 7/1997 | Libin |
| 5,648,064 A | 7/1997 | Gaffar et al. |
| 5,690,913 A | 11/1997 | Hsu et al. |
| 5,698,182 A | 12/1997 | Prencipe et al. |
| 5,713,738 A | 2/1998 | Yarborough |
| 5,718,886 A | 2/1998 | Pellico |
| 5,725,843 A | 3/1998 | Fischer |
| 5,746,598 A | 5/1998 | Fischer |
| 5,766,011 A | 6/1998 | Sibner |
| 5,766,574 A | 6/1998 | Christina-Beck et al. |
| 5,770,105 A | 6/1998 | Fischer |
| 5,785,527 A | 7/1998 | Jensen et al. |
| 5,785,957 A | 7/1998 | Losee et al. |
| 5,814,304 A | 9/1998 | Wong et al. |
| 5,851,514 A | 12/1998 | Hassan |
| 5,858,332 A | 1/1999 | Jensen et al. |
| 5,902,568 A | 5/1999 | Ryles |
| 5,922,307 A | 7/1999 | Montgomery |
| 5,928,628 A | 7/1999 | Pellico |
| 5,985,249 A | 11/1999 | Fischer |
| 6,036,493 A | 3/2000 | Sharma |
| 6,036,943 A | 3/2000 | Fischer |
| 6,086,855 A | 7/2000 | Fischer |
| 6,106,293 A | 8/2000 | Wiesel |
| 6,106,812 A | 8/2000 | Prencipe et al. |
| 6,149,895 A | 11/2000 | Kutsch |
| 6,312,670 B1 | 11/2001 | Montgomery |
| 6,312,671 B1 * | 11/2001 | Jensen et al. ............. 424/53 |
| 6,322,773 B1 | 11/2001 | Montgomery |
| 6,322,774 B1 * | 11/2001 | Jensen et al. ............. 424/53 |
| 6,365,134 B1 * | 4/2002 | Orlowski et al. ............. 424/53 |
| 6,447,757 B1 * | 9/2002 | Orlowski et al. ............. 424/53 |
| 6,488,913 B1 * | 12/2002 | Orlowski et al. ............. 424/53 |

* cited by examiner

PROCESS AND COMPOSITION FOR HIGH EFFICACY TEETH WHITENING

RELATED APPLICATION DATA

This application is a Continuation-in-Part of U.S. patent application Ser. No. 10/114,436 filed Apr. 1, 2002, now abandoned which is a Continuation of U.S. patent application Ser. No. 09/618,567, filed Jul. 17, 2000, now U.S. Pat. No. 6,365,134, which is a Continuation of U.S. patent application Ser. No. 09/348,456, filed Jul. 7, 1999, now abandoned, the disclosures of which are hereby incorporated by reference herein in their entireties.

FIELD OF THE INVENTION

This invention relates to a method and composition for high efficacy teeth whitening which is a two-part composition, with one part containing carbamide peroxide and the other containing salts, oxides or hydroxides of metals belonging to the first or second group of the Periodic Table.

BACKGROUND OF THE INVENTION

Teeth whiteners, also known as teeth bleaching agents, are in widespread use as a cosmetic means to enhance appearance and, generally, to contribute to better oral health and hygiene.

Particularly popular and most effective among these devices are those whose chemistry is based on peroxides, of which hydrogen peroxide and carbamide peroxide (representing an adduct of hydrogen peroxide and urea) are most frequently employed. Such peroxides are characterized by their lack of stability resulting in the generation of radical (atomic) oxygen, the chemical action of which is responsible for the desired whitening/bleaching effect. The generation of atomic oxygen is, however, highly undesirable during storage of such peroxide-based teeth whitening devices. Thus, in their commercial form, such devices are formulated in a manner which attempts to inhibit premature peroxide decomposition. Contact with certain foreign objects, especially materials having highly developed surface areas; certain chemicals; and elevated pH accelerate the decomposition process of said peroxides and the liberation of radical oxygen.

Stability of such formulations, however, is in direct conflict with the purpose and object of their applications, namely achieving the best possible whitening effect in the shortest possible time of contact with the tooth surface. Consequently, teeth whitening devices of prior art formulations typically require multiple applications stretching over a period of weeks and even months, with each recommended application time usually being from two to eight hours.

Of the two forms of peroxides commonly used in commercial teeth whiteners, hydrogen peroxide is preferred for its faster action, while carbamide peroxide based formulations offer advantages in terms of greater storage stability, more desirable consistencies and handling properties, and less risk of damage to soft tissues. Stability of both hydrogen peroxide and carbamide peroxide-based formulations is greater, especially in the case of the former, at low pH, preferably in the range of 3–4.5. Carbamide peroxide based materials may, however, exhibit adequate stability even at neutral or near neutral pH. This makes such formulations more desirable from the standpoint of better perceived compatibility with mucosa and of having no or negligible detrimental effect on tooth enamel and on the health of teeth that are in less than intact condition.

Carbamide peroxide formulations are particularly stable in environments containing little or no water. Examples of carriers for carbamide peroxide most common to commercial use are glycerin and propylene glycol. While these carriers are considered nontoxic and convenient for their compatibility with desirable additives such as thickening agents, preservatives, flavors and therapeutics, their use may create some unwelcome, though generally minor, side effects. The most common side effect is discomfort caused by the desiccating effect of anhydrous (or nearly anhydrous) hydrophilic solvents/carriers on mucosa, especially pronounced when scarified or inflamed tissue is involved. Similar responses may also be expected in cases of leaching restorations or recessed gums.

Attempts have been made to accelerate the teeth beaching processes without increasing the concentration of the peroxide by using heat-generating devices, such as high intensity light emitting instruments or lasers. Because of the cost of necessary equipment and greatly increased risk of tissue damage associated with these techniques, they are designed for use exclusively by a dentist. Such treatments are necessarily expensive. The most effective of these techniques are those using lasers, but they also carry the highest possibility of inflicting damage on the teeth and/or soft tissue. The cost of treatments is considerably higher than when conventional methods are used.

SUMMARY OF THE INVENTION

In accordance with one embodiment, there is provided a composition for whitening teeth. The composition comprises a first component in the form of a suspension or solution comprising about 15% to 34% carbamide peroxide and up to 50% water, said first component having a pH of about 3.0 to 7.5; and a second component in the form of an aqueous gel or paste comprising one or more alkali materials selected from the group consisting of: oxides and/or hydroxides of metals belonging to the first or second group of the Periodic Table including, but not limited to, sodium, potassium, magnesium and/or calcium; and sodium, potassium, calcium, or magnesium salts of weak acids; said second component having a pH of about 8.0 to 12; wherein admixing of said first and second components prior to applying the composition to the teeth provides the composition for whitening teeth having a pH of about 8.0 to 12.

In accordance with another embodiment, there is provided a composition for whitening teeth. The process comprises a first component in the form of a suspension or solution, said first component having a pH of about 3.0 to 7.5 and comprising about 15% to 34% carbamide peroxide, up to about 50% water, and at least one stabilizer, said first component being substantially colorless; and a second component in the form of an aqueous gel or paste, said second component having a pH of about 8.0 to 12 and comprising one or more alkali materials selected from the group consisting of oxides and/or hydroxides of metals belonging to the first or second group of the Periodic Table including, but not limited to, sodium, potassium, magnesium and/or calcium; and sodium, potassium, calcium, or magnesium salts of weak acids, and a colored dye indicator which gradually discolors or loses color when reacted with a radical oxygen; wherein admixing of said first and second components prior to applying the composition to teeth provides the composition for whitening teeth having a pH of about 8.0 to 12.

In further embodiments, the first component, the second component, or both the first and second components further includes a thickening agent. Preferably, the thickening agent is selected from the group of polyacrylic acid, polyacrylic acid salts, amine crosslinked polyacrylic acid, natural gums, gelatin, starch, cellulose derivatives, polyalkylene oxides, and combinations thereof. In a further embodiment, the composition includes sodium fluoride, stannous fluoride, or sodium monofluorophosphate, which may be present in either or both parts.

In accordance with yet another embodiment, there is provided a process for whitening teeth. The process comprises mixing first and second components to form a tooth whitening composition and contacting one or more teeth with the tooth whitening composition for about 10–60 minutes or less. The first component of the composition comprises about 15% to 34% carbamide peroxide and up to 50% water, said first component having a pH of about 3.0 to 7.5; and the second component comprises one or more alkali materials selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate, and has a pH of about 8.0 to 10. Further embodiments may comprise one or more of the following: the contacting one or more teeth with the tooth whitening composition occurs for about 20 minutes; the tooth whitening composition is placed into a flexible tray or form shaped to fit over one or more teeth in a human mouth prior to contacting said teeth with the composition; and/or the teeth may be separated from the composition after a dye indicator discolors or loses color.

In one embodiment, the first component and the second component are mixed in a ratio of 1:1. In a further embodiment, the alkali materials are selected from the group of: calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate.

In a preferred embodiment, the first component is substantially colorless and the second component includes a colored dye indicator which gradually discolors or loses color when reacted with a radical oxygen.

If included in a formulation, preferred stabilizers include sodium silicate, 8-hydroxyquinoline, sodium stannate, oxalic-bis(cyclohexylidene-hydrazide), amino-trismethylene-phosphonic acid, 2-phosphonobutane-1,2,4-tricarboxylic acid, sodium pyrophosphate, and 1-hydroxyethylidene-1,1-phosphonic acid.

DETAILED DESCRIPTION OF THE PREFERRED EMBODIMENTS

The description which follows provides preferred embodiments of two part teeth whitening or bleaching systems. The scope of the invention presently disclosed extends beyond the embodiments and examples presented herein, which are merely exemplary. All percentages set forth herein are by weight unless stated otherwise.

In preferred embodiments, the composition comprises two component parts which are separated from each other during storage, but are mixed shortly or immediately before their application. When mixed, the two parts form a composition for which desired whitening effects are achieved in a fraction of the time required by prior art formulations. Furthermore, as compared to prior art formulations, the methods and compositions disclosed herein provide for greatly reduced user discomfort caused by the desiccation or irritation of soft oral tissues and the virtual elimination of the deleterious effects on tooth enamel caused by the low pH.

The teeth whitening compositions preferably comprise two parts. The first part comprises carbamide peroxide (i.e. hydrogen peroxide in the form of an adduct with urea), dissolved or suspended in a suitable solvent/carrier such as water, glycerin, or propylene glycol. The first part may also comprise at least one stabilizer. In one embodiment, the first part includes a stabilizer when the first part contains more than 15% carbamide peroxide. In a further embodiment, if the first part contains more than 5% water, at least one stabilizer is added.

The carbamide peroxide in the first part is preferably present at a concentration from about 5% to about 40%, including about 15% to about 34%, including 16%, 17%, 18%, 19%, 20%, 21%, 22%, 23%, 24%, 25%, 26%, 27%, 28%, 29%, 30%, 31%, 32%, and 33%. In embodiments in which water is present in the first part, the carbamide peroxide is preferably present at concentrations of about 15% or greater, as noted above.

If water is present in the first component, it is preferably present at concentrations up to about 50%. In a preferred embodiment, water is present in the first component at a concentration of about 5% to about 35%, including 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, and 34%.

Although use of a stabilizer in the first part is not necessary because the components will be stable for a significant period of time without stabilizers, in some embodiments, one or more stabilizers are added to increase the shelf-life of the product. Addition of a stabilizer is preferred in those embodiments comprising more than 5% water, particularly more than 10% water and/or more than 15% carbamide peroxide. Although addition of a stabilizer is preferred in such embodiments, it is not a necessary component.

Suitable stabilizers include, but are not limited to, sodium silicate, 8-hydroxyquinoline, sodium stannate, oxalic-bis (cyclohexylidene-hydrazide), amino-trismethylene-phosphonic acid, 2-phosphonobutane-1,2,4-tricarboxylic acid, sodium pyrophosphate, and 1-hydroxyethylidene-1,1-phosphonic acid. If present, stabilizers are preferably at a concentration of from about 0.05% to about 5.0%, including 0.1%, 0.25%, 0.4%, 0.5%, 0.75%, 0.9%, 2.5%, 3%, 3.5%, 4%, and 4.5%. In one embodiment, the stabilizer is at a concentration of from about 1.0% to about 2.0%, including 1.2%, 1.3%, 1.4%, 1.5%, 1.6%, 1.7%, 1.8% and 1.9%. When sodium pyrophosphate is used as a stabilizer, it is preferably present at a concentration of from about 1.0% to about 2.0%. When 1-hydroxyethylidene-1,1-phosphonic acid is used as a stabilizer, it is preferably present at a concentration of from about 0.1% to about 2.0%. When amino-trismethylene-phosponic acid is used as a stabilizer, it is preferably present at a concentration of from about 0.05% to about 0.20%.

Suitable thickeners may be added to such a mixture to achieve a desirable consistency to facilitate application and to slow the dissolution process in order to prolong the bleaching or whitening action.

In one embodiment, carriers such as glycerin, ethyl alcohol, propylene glycol and polyalkylene glycols are used for formulations based on carbamide peroxide in which the first component is anhydrous. Such carriers may also be included in the first component when water is included in the first component.

The second component of the teeth bleaching or whitening system of this invention is preferably of a gel or paste consistency. In preferred embodiments, water is used as the carrier, either with or without additional carriers, and serves as a medium in which salts, oxides and/or hydroxides of metals belonging to the first or second group of the Periodic Table including, but not limited to, sodium, potassium, magnesium and/or calcium are dissolved or suspended. Oxides or hydroxides of sodium, potassium, calcium and magnesium were found to be particularly suitable as components of preferred formulations. Among salts of the type noted, those containing anions derived from weak acids such as acetic, acrylic, glutaric, methacrylic, etc. are preferred.

In one embodiment, the formulation further comprises fluoride salts such as stannous fluoride, sodium monofluorophosphate or sodium fluoride. Such salts may be add additional benefits to the teeth treatments.

Common thickening and suspending agents may be incorporated into either or both of the first and second components to achieve a desired consistency of the system components. Preferred thickening agents include, but are not limited to, alkaline salts of polyacrylic acid, amine crosslinked polyacrylic acid, polyethylene oxide, cellulose derivatives, water soluble natural gums, gelatin and starch.

Flavoring and coloring agents may be added to enhance the acceptance or appeal of the material. Additionally, coloring agents may be added as indicators of the progress of radical oxygen generation and the reactivity of peroxide. Desirable flavors may include, among others, food grade orange, lemon, peppermint, spearmint, mint, bubble gum, cherry, watermelon, strawberry and apple varieties. Desirable coloring agents include any water soluble dyes, including, but not limited to FD&C or D&C water soluble dyes, such as FD&C Blue #1, FD&C Blue #2, FD&C Green #3, FD&C Red #3, FD&C Yellow #5, and FD&C Yellow #6, as well as Grape color extract, and beta-carotene. The coloring and/or flavoring agents are preferably, but not necessarily, incorporated in the second part of the system, i.e., the part not containing peroxides. If coloring agents or dyes are used as indicators, it is preferred that the part not containing the dye indicator or coloring agent is substantially colorless, including clear and white and varying degrees of opacity therebetween.

The pH of the first part or component, i.e. that containing the peroxide, is preferably in the range of about pH 3–7.5. In one embodiment, the pH is preferably about 3.5–5.5, including, but not limited to: 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, and 5.4. The pH of the second part, is preferably above pH 8. In one embodiment, the pH is preferably in the range of about 9–12, including, but not limited to:9.1, 9.2, 9.3, 9.4, 9.5, 9.6, 9.7, 9.8, 9.9, 10, 10.2, 10.4, 10.6, 10.8, 10.9, 11, 11.2, 11.4, 11.6, 11.8, and 11.9. The pH of each part may be set or maintained by the use of acids, bases, and buffers, as appropriate. The mixture of the parts, at proportions as indicated for use, preferably have pH values of about 8–12, preferably 8.5–10.5, including, but not limited to: 8.6, 8.7, 8.8, 8.9, 9.0, 9.1, 9.2, 9.3, 9.4, 9.5, 9.6, 9.7, 9.8, 9.9, 10, 10.1, 10.2, 10.3, and 10.4.

The teeth bleaching systems according to preferred embodiments are more effective than those in the past when difficult to whiten teeth are involved. The systems are faster in their bleaching action, thus allowing for shorter application times or less frequent applications while delivering superior results. It was also unexpectedly found that the present teeth bleaching systems are very well tolerated by the soft oral tissue and are unlikely to irritate mucosa or cause discomfort. Astonishingly good appearance and good health of teeth after bleaching may also attributed to the presence of mineralizing agents such as calcium salts in preferred embodiments.

It was also unexpected to find that oral tissue can tolerate elevated pH of about 8.5–11.5 as is found in some embodiments for the short periods of time sufficient to achieve easily noticeable teeth whitening effects. Obtaining comparable results using conventional teeth whitening materials generally require application times up to 100 times longer.

EXAMPLES AND PROPERTIES OF THE TEETH WHITENING FORMULATIONS

Some preferred embodiments are illustrated in Examples 1–5 below.

Example 1

The teeth bleaching system consisted of:

| Part 1: | |
|---|---|
| carbamide peroxide | 22% |
| glycerin | 76.8% |
| partially neutralized polycarboxylic acid | 2.2% |
| Part 2: | |
| water | 63% |
| calcium carbonate | 9% |
| sodium carbonate | 1.8% |
| sodium bicarbonate | 3% |
| FD&C Blue #1 | 0.2% |
| silica | 4% |
| carboxymethyl cellulose | 3% |
| glycerin | 16% |

The parts were mixed together at a volumetrically 1:1 ratio. The pH of the mixture was 10.8. The rate of generation of free oxygen was tested by redox colorimetric method at body temperatures of 37° C. It was found that the generation of radical oxygen was an order of magnitude faster in the two component system than in a system comprising Part 1 only. The blue color indicator in Part 2 remained unchanged even after six weeks of exposure at 37° C. When the indicator was added to Part 1 instead of Part 2, the color still remained pronounced after 72 hours exposure at 37° C. However, after mixing Part 1 and Part 2 together, the color disappeared after one hour.

Clinical studies have confirmed the fast action and high efficacy of this material with no adverse reaction reported and excellent patient acceptance. In a particular clinical case the shade of the treated teeth changed in a single session from Vita C4 to C1 within 20 minutes after application.

Example 2

The bleaching system consisted of:

| Part 1: | |
|---|---|
| carbamide peroxide | 16% |
| glycerin | 76.7% |
| partially neutralized polycarboxylic acid | 2.3% |
| water | 5% |
| Part 2: | |
| water | 64% |
| glycerin | 16% |
| carboxymethyl cellulose | 3.8% |
| calcium carbonate | 8.5% |
| sodium bicarbonate | 1.5% |
| sodium carbonate | 0.5% |
| sodium fluoride | 0.5% |
| FD&C Blue #1 | 0.2% |
| silica | 5% |

When Part 1 and Part 2 were mixed together (at a 1:1 ratio by volume), the color disappeared within 5 hours. Clinical experience with this material is similar to that described for Example 1.

Example 3

| Part 1: | |
|---|---|
| carbamide peroxide | 22% |
| glycerin | 76.8% |
| partially neutralized polycarboxylic acid | 2.2% |
| Part 2: | |
| water | 67% |
| glycerin | 15% |
| calcium carbonate | 7% |
| potassium bicarbonate | 2% |
| carboxymethyl cellulose | 3% |
| xanthum gum | 0.3% |
| silica | 5.7% |

The materials above were mixed at a ratio of 1:1 volumetrically. The overall performance of this formulation was substantially similar to that of Example 2.

The following examples identify that the first part of the composition may be also mixed in a carrier comprising water, with or without the presence of a stabilizer.

Example 6

| Part 1: | |
|---|---|
| Sodium pyrophosphate decahydrate | 1.00% |
| Polyacrylic acid | 0.15% |
| Deionized water | 27.00% |
| 1,2-propylene glycol | 27.00% |
| 1-hydroxyethylidene-1, 1-phosphonic acid | 0.10% |
| Phosphoric acid | 0.31% |
| Carbamide peroxide | 30.00% |
| Polyethylene oxide | 14.44% |
| Part 2: | |
| Glycerin | 19.94% |
| Hydroxypropyl cellulose | 2.51% |
| Deionized water | 62.84% |
| Sodium carbonate | 1.05% |
| Sodium bicarbonate | 2.65% |
| Xylitol | 4.40% |
| Polyethylene oxide | 3.14% |
| Silica | 2.93% |
| Peppermint oil | 0.52% |
| FD&C Blue #1 | 0.02% |

The two components were mixed in a 1:1 ratio by volume. The pH of the mixture was 9.3 at 26.5° C. The blue color of the indicator disappeared entirely in twenty-four (24) minutes.

Example 7

| Part 1: | |
|---|---|
| Sodium pyrophosphate decahydrate | 0.050% |
| Polyacrylic acid | 0.300% |
| Deionized water | 32.500% |
| 1,2-propylene glycol | 32.500% |
| 1-hydroxyethylidene-1, 1-phosphonic acid | 0.045% |
| Phosphoric acid | 0.080% |
| Carbamide peroxide | 22.050% |
| Polyethylene oxide | 12.475% |
| Part 2: | |
| Glycerin | 19.58% |
| Hydroxypropyl cellulose | 2.51% |
| Deionized water | 62.84% |
| Sodium carbonate | 1.05% |
| Sodium bicarbonate | 2.65% |
| Xylitol | 4.40% |
| Polyethylene oxide | 3.14% |
| Silica | 2.93% |
| Peppermint oil | 0.52% |
| FD&C Blue #1 | 0.02% |

The two components were mixed in a 1:1 ratio by volume. The pH of the mixture was 9.2 at 26.5° C. The blue color disappeared entirely in twenty-one (21) minutes.

Example 8

| Part 1: | |
|---|---|
| Sodium carbonate | 0.48% |
| Polyacrylic acid | 0.30% |
| Deionized water | 5.00% |
| 1,2-propylene glycol | 59.00% |
| Phosphoric acid | 0.26% |
| Carbamide peroxide | 22.00% |
| Peppermint oil | 0.40% |
| Polyethylene oxide | 12.56% |
| Part 2: | |
| Glycerin | 19.58% |
| Hydroxypropyl cellulose | 2.51% |
| Deionized water | 62.84% |
| Sodium carbonate | 1.05% |
| Sodium bicarbonate | 2.65% |
| Xylitol | 4.40% |
| Polyethylene oxide | 3.14% |
| Silica | 2.93% |
| Peppermint oil | 0.52% |
| FD&C Blue #1 | 0.02% |

The two components were mixed in a 1:1 ratio by volume. The pH of the mixture was 9.3 at 26.5° C. The blue color disappeared entirely in twenty-two (22) minutes.

The various methods, techniques and compositions described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A composition for whitening teeth comprising:
   a first component in the form of a suspension or solution comprising about 5% to 34% carbamide peroxide and up to 50% water, and at least one stabilizer selected from the group consisting of sodium silicate, 8-hydroxyquinoline, sodium stannate, oxalic-bis (cyclohexylidenehydrazie), amino-trismethylene-phosphonic acid, 2- phosphonobutane-1,2,4-tricarboxylic acid, sodium pyrophosphate, and 1-hydroxyethylidene1,1-phosphonic acid, said first component having a pH of about 3.0 to 7.5; and
   a second component in the form of an aqueous gel or paste comprising one or more alkali materials selected from the group consisting of: oxides of metals belonging to the first or second group of the Periodic Table, hydroxides of metals belonging to the first or second group of the Periodic Table, and sodium, potassium, calcium, or magnesium salts of weak acids; said second component having a pH of about 8.0 to 12;
   wherein admixing of said first and second components prior to applying the composition to teeth provides the composition for whitening teeth having a pH of about 8.0 to 12.

2. The composition of claim 1, wherein the first component comprises more than 5% water.

3. The composition of claim 1, wherein the first component, the second component, or both the first and second components further comprise one or more thickening agents.

4. The composition of claim 3, wherein the one or more thickening agents are independently selected from the group consisting of polyacrylic acid, polyacrylic acid salts, amine crosslinked polyacrylic acid, natural gums, gelatin, starch, cellulose derivatives, and polyalkalene oxides.

5. The composition of claim 1, wherein the composition further comprises sodium fluoride, stannous fluoride, or sodium monofluorophosphate.

6. The composition of claim 1, wherein the ratio of mixing of the first component to the second component is 1:1 by volume.

7. The composition of claim 1, wherein said alkali materials are selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate.

8. A composition for whitening teeth comprising:
   a first component in the form of a suspension or solution, said first component having a pH of about 3.0 to 7.5 and comprising about 15% to 34% carbamide peroxide, up to about 50% water, and at least one stabilizer, selected from the group consisting of sodium silicate, 8-hydroxyquinoline, sodium stannate, oxalic-bis (cyclohexylidenehydrazide), amino-trismethylene-phosphonic acid, 2-phosphonobutane-1,2,4-tricarboxylic acid, sodium pyrophosphate, and 1-hydroxyethylidene-1,1-phosphonic acid, said first component being colorless; and
   a second component in the form of an aqueous gel or paste, said second component having a pH of about 8.0 to 12 and comprising one or more alkali materials selected from the group consisting of oxides of metals belonging to the first or second group of the Periodic Table, hydroxides of metals belonging to the first or second group of the Periodic Table, and sodium, potassium, calcium, or magnesium salts of weak acids, and a colored dye indicator which gradually discolors or loses color when reacted with a radical oxygen;
   wherein admixing of said first and second components prior to applying the composition to teeth provides the composition for whitening teeth having a pH of about 8.0 to 12.

9. The composition of claim 8, wherein the first component comprises more than 5% water.

10. The composition of claim 8, wherein the first component, the second component, or both the first and second components further comprise one or more thickening agents.

11. The composition of claim 8, wherein the one or more thickening agents are independently selected from the group consisting of polyacrylic acid, polyacrylic acid salts, amine crosslinked polyacrylic acid, natural gums, gelatin, starch, cellulose derivatives, and polyalkalene oxides.

12. The composition of claim 8, wherein the composition further comprises sodium fluoride, stannous fluoride, or sodium monofluorophosphate.

13. The composition of claim 8, wherein the ratio of mixing of the first component to the second component is 1:1.

14. The composition of claim 8, wherein said alkali materials are selected from the group consisting of: calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate.

15. A process for whitening teeth, comprising:
   mixing first and second components to form a tooth whitening composition,
      the first component comprising about 15% to 34% carbamide perioxide and up to 50% water, and at least one stabilizer selected from the group consisting of sodium silicate, 8-hydroxyquinoline, sodium stannate, oxalic-bis (cyclohexylidenehydrazide), amino-trismethylene-phosphonic acid, 2-phosphonobutane-1,2,4-tricarboxylic acid, sodium pyrophosphate, and 1-hydroxyethylidene-1,1,-phosphonic acid, said first component having a pH of about 3.0 to 7.5; and
      the second component comprising one or more alkali materials selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate, said second component having a pH of about 8.0 to 10; and
   contacting one or more teeth with the tooth whitening composition for about 10–60 minutes or less.

16. The process according to claim 15, wherein contacting one or more teeth with the tooth whitening composition occurs for about 20 minutes.

17. The process according to claim 15, further comprising placing the tooth whitening composition into a flexible tray or form shaped to fit over one or more teeth in a human mouth prior to contacting said teeth with the composition.

18. The process according to claim 15, wherein the second component further comprises a dye indicator and the process further comprises separating the composition from the teeth after the dye indicator discolors or loses color.

19. The process according to claim 18, wherein the first part is colorless.

20. The process of claim 15, wherein the first component comprises more than 5% water.

21. The composition of claim 1, wherein said one or more alkali materials include one or more alkali materials selected from the group consisting of bicarbonate, acetate, carbonate, benzoate, acrylate, methacrylate, gluconate, phosphate, and silicate salts.

22. The composition of claim 8, wherein said one or more alkali materials include one or more alkali materials selected from the group consisting of bicarbonate, acetate, carbonate, benzoate, acrylate, methacrylate, gluconate, phosphate, and silicate salts.

23. A composition for whitening teeth comprising:
    a first component in the form of a suspension or solution comprising about 5% to 34% carbamide peroxide and up to 50% water, and at least one stabilizer selected from the group consisting of sodium silicate, 8-hydroxyquinoline, sodium stannate, oxalic-bis (cyclohexylidenehydrazide), amino-trismethylene-phosphonic acid, 2-phosphonobutane-1,2,4-tricarboxylic acid, sodium pyrophosphate, and 1-hydroxyethylidene-1,1-phosphonic acid, said first component having a pH of about 3.0 to 7.5; and
    a second component in the form of an aqueous gel or paste comprising one or more alkali materials selected from the group consisting of sodium, potassium, magnesium, and calcium salts of weak acids, oxides of sodium, potassium, magnesium, and calcium; and hydroxides of sodium, potassium, magnesium, and calcium; said second component having a pH about 8.0;
    wherein admixing of said first and second components prior to applying the composition to the teeth provides the composition for whitening teeth having a pH of about 8.0 to 12.

24. The composition of claim 23, wherein said one or more alkali materials include one or more alkali materials selected from the group consisting of bicarbonate, acetate, carbonate, benzoate, acrylate, methacrylate, gluconate, phosphate, and silicate salts.

25. The composition of claim 23, wherein the first component comprises more than 5% water.

26. The composition of claim 23, wherein the first component, the second component, or both the first and second components further comprise one or more thickening agents.

27. The composition of claim 26, wherein the one or more thickening agents are independently selected from the group consisting of polyacrylic acid, polyacrylic acid salts, amine crosslinked polyacrylic acid, natural gums, gelatin, starch cellulose derivatives, and polyalkylene oxides.

28. The composition of claim 23, wherein the composition further comprises sodium fluoride, stannous fluoride or sodium monofluorophosphate.

29. The composition of claim 23, wherein a ratio of mixing of the first component to the second component is about 1:1 by volume.

30. The composition of claim 23, wherein said alkali materials are selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate.

31. A composition for whitening teeth comprising:
    a first component in the form of a suspension or solution, said first component having a pH of about 3.0 to 7.5 and comprising about 15% to 34% carbamide peroxide, up to about 50% water, and at least one stabilizer selected from the group consisting of sodium silicate, 8-hydroxyquinoline, sodium stannate, oxalic-bis (cyclohexylidenehydrazide), amino-trismethylene-phosphonic acid, 2-phosphonobutane-1,2,4-tricarboxylic acid, sodium pyrophosphate, and 1-hydroxyethylidene-1,1-phosphonic acid, said first component being colorless; and
    a second component in the form of an aqueous gel or paste, said second component having a pH above 8.0 and comprising a colored dye indicator which gradually discolors or loses color when reacted with a radical oxygen, and one or more alkali materials selected from the group consisting of sodium, potassium, magnesium, and calcium salts of weak acids, oxides of sodium, potassium, magnesium, and calcium, and hydroxides of sodium, potassium, magnesium, and calcium;
    wherein admixing of said first and second components prior to applying the compositon to teeth provides the composition for whitening teeth having a pH of about 8.0 to 12.

32. The composition of claim 31, wherein said one or more alkali materials include one or more alkali materials selected from the group consisting of bicarbonate, acetate, carbonate, benzoate, acrylate, methacrylate, gluconate, phosphate, and silicate salts.

33. The composition of claim 31, wherein the first component comprises more than 5% water.

34. The composition of claim 31, wherein the first component, the second component, or both the first and second components further comprise one or more thickening agents.

35. The composition of claim 31, wherein the one or more thickening agents are independently selected from the group consisting of polyacrylic acid, polyacrylic acid salts, amine crosslinked polyacrylic acid, natural gums, gelatin, starch, cellulose derivativs, and polyalkylene oxides.

36. The composition of claim 31, wherein the composition further comprises sodium fluoride, stannous fluoride, or sodium monofluorophosphate.

37. The composition of claim 31, wherein a ratio of mixing of the first component to the second component is 1:1.

38. The composition of claim 31, wherein said alkali materials are selected from the group consisting of calcium oxide, sodium hydroxide, potassium hydroxide, potassium bicarbonate, sodium acetate, sodium carbonate, sodium bicarbonate, sodium benzoate, sodium acrylate, sodium methacrylate, sodium gluconate, calcium carbonate, magnesium carbonate, calcium phosphates, calcium bicarbonate, calcium gluconate, and calcium silicate.

* * * * *